US012343121B2

(12) United States Patent
Corradini et al.

(10) Patent No.: US 12,343,121 B2
(45) Date of Patent: Jul. 1, 2025

(54) SYSTEM AND METHOD FOR DETECTING VITAL PHYSIOLOGICAL PARAMETERS OF A SUBJECT

(71) Applicant: Università degli Studi di Modena e Reggio Emilia, Modena (IT)

(72) Inventors: Matteo Corradini, Modena (IT); Sergio Fonda, Modena (IT); Andrea Malagoli, Modena (IT)

(73) Assignee: Università Degli Studi Di Modena E Reggio Emilia, Modena (IT)

(*) Notice: Subject to any disclaimer, the term of this patent is extended or adjusted under 35 U.S.C. 154(b) by 96 days.

(21) Appl. No.: 16/495,906

(22) PCT Filed: Mar. 21, 2018

(86) PCT No.: PCT/IB2018/051901
§ 371 (c)(1),
(2) Date: Sep. 20, 2019

(87) PCT Pub. No.: WO2018/172958
PCT Pub. Date: Sep. 27, 2018

(65) Prior Publication Data
US 2020/0029836 A1    Jan. 30, 2020

(30) Foreign Application Priority Data
Mar. 23, 2017   (IT) .................. 102017000031915

(51) Int. Cl.
A61B 5/00       (2006.01)
A61B 5/01       (2006.01)
(Continued)

(52) U.S. Cl.
CPC ........ A61B 5/02055 (2013.01); A61B 5/0006 (2013.01); A61B 5/01 (2013.01);
(Continued)

(58) Field of Classification Search
CPC . A61B 5/0241; A61B 5/02125; A61B 5/7239; A61B 5/02055; A61B 5/318;
(Continued)

(56) References Cited

U.S. PATENT DOCUMENTS

2007/0225609 A1* 9/2007 Rosch ............... A61B 5/02125
                                              600/485
2008/0214942 A1* 9/2008 Oh .................... A61B 5/02427
                                              600/485
(Continued)

FOREIGN PATENT DOCUMENTS

GB      2546774 A   *  8/2017  .......... A61B 5/0002
WO      2015171667 A1   11/2015
WO      WO-2016155348 A1 * 10/2016  ......... A61B 5/02125

OTHER PUBLICATIONS

Plácido da Silva, H., "Check Your Biosignals Here: A new dataset for off-the-person ECG biometrics," Computer Methods and Programs in Biomedicine 113, pp. 503-514 (2014).
(Continued)

Primary Examiner — Sana Sahand
(74) Attorney, Agent, or Firm — Elmore Patent Law Group, P.C.; Joseph C. Zucchero; Carolyn S. Elmore

(57) ABSTRACT

A system (1) for detecting vital physiological parameters of a subject (10), comprising support means (15) which can be associated with the subject (10) and are connected to acquisition means (20) configured to acquire synchronously an ECG signal and a PPG signal of the subject (10); the system (1) comprises processing means (40) which are connected to the acquisition means (20), the processing means (40) comprising a systolic and diastolic arterial pressure module (43) configured to calculate a vital physiological parameter related to systolic and diastolic arterial pressure, which can be transmitted to at least one telematic device (5) by way of (Continued)

transceiver means (60) configured to transmit the vital physiological parameter toward the telematic device (5).

3 Claims, 2 Drawing Sheets

(51) Int. Cl.
*A61B 5/0205* (2006.01)
*A61B 5/145* (2006.01)
*A61B 5/33* (2021.01)
*A61B 5/021* (2006.01)
*A61B 5/024* (2006.01)
*A61B 5/08* (2006.01)

(52) U.S. Cl.
CPC ............ *A61B 5/14542* (2013.01); *A61B 5/33* (2021.01); *A61B 5/021* (2013.01); *A61B 5/02416* (2013.01); *A61B 5/0816* (2013.01)

(58) Field of Classification Search
CPC ..... A61B 5/0006; A61B 5/01; A61B 5/14542; A61B 5/021; A61B 5/02416; A61B 5/0816; A61B 5/02108; A61B 5/6895; A61B 2503/10
See application file for complete search history.

(56) References Cited

U.S. PATENT DOCUMENTS

| | | | |
|---|---|---|---|
| 2010/0130876 A1* | 5/2010 | Cho | A61B 5/0285 600/490 |
| 2011/0009754 A1 | 1/2011 | Wenzel et al. | |
| 2012/0029320 A1* | 2/2012 | Watson | A61B 5/02416 600/301 |
| 2014/0073969 A1* | 3/2014 | Zou | A61B 5/346 600/479 |
| 2014/0142445 A1 | 5/2014 | Banet et al. | |
| 2015/0119725 A1* | 4/2015 | Martin | A61B 5/021 600/479 |
| 2017/0079591 A1* | 3/2017 | Gruhlke | A61B 5/7278 |
| 2017/0150891 A1* | 6/2017 | Tsuchimoto | A61B 5/0205 |
| 2017/0164856 A1* | 6/2017 | Baxi | A61B 5/6898 |
| 2017/0281012 A1* | 10/2017 | Kacelenga | A61B 5/6897 |
| 2018/0085058 A1* | 3/2018 | Chakravarthi | A61B 5/150022 |

OTHER PUBLICATIONS

Payne, R.A., "Pulse transit time measured from the ECG: an unreliable marker of beat-to-beat blood pressure," J. Appl Physiol 100: pp. 136-141 (2006).

Malagoli, A., et al., "Towards a method for the objective assessment of cognitive workload," A pilot study in Vessel Traffic Service (VTS) of maritime domain, Universita Modena. Downloaded on Sep. 13, 2024.

Proença, J., et al., "Is Pulse Transit Time a good indicator of Blood Pressure changes during short physical exercise in a young population?" 32 Annual International Conference of the IEEE EMBS Buenos Aires Argentina, Aug. 31-Sep. 4, 2010 (Universita Modena. Downloaded on Aug. 5, 2024).

Pereira, T.M.C., et al., "Biometric Recognition: A Systematic Review on Electrocardiogram Data Acquisition Methods," Sensors, 23, pp. 1-31 (2023).

* cited by examiner

SYSTEM AND METHOD FOR DETECTING VITAL PHYSIOLOGICAL PARAMETERS OF A SUBJECT

This application claims priority to International Application Serial No. PCT/IB2018/051901, filed on Mar. 21, 2018, which claims the benefit of Italian Patent Application Serial No. 102017000031915, filed on Mar. 23, 2017. The contents of the above applications are incorporated by reference as if fully set forth herein in their entirety.

The present invention relates to a system and a method for detecting vital physiological parameters of a subject, which are particularly but not exclusively useful and convenient in the healthcare sector, in the sports sector and in the automotive sector.

In the healthcare sector, the detection of the vital physiological parameters of a subject is particularly essential in order to perform first aid interventions, in order to assess the severity of a disease or of an injury and in order to monitor the state of health of a subject suitable to carry out work or sports activities.

It is normally thought that detecting vital physiological parameters is an activity that can be performed only in ordinary hospitalization wards by highly trained staff. The vital physiological parameters are, in fact, usually useful to healthcare professionals, who, in hospital facilities, take care of the sick or injured subject.

However, said vital physiological parameters are particularly useful also to those who happen to give first aid and have no medical training.

Moreover, also in the sports sector detecting vital physiological parameters of a subject is necessary to analyze the physiological reactions of a subject based on the different activities performed. In this manner it is possible, therefore, to manage and improve one's own sports performance in order to obtain better results, saving any losses of psycho-physical energies and limiting any unsuitable behaviors that would worsen the physical conditions of the subject.

Detecting vital physiological parameters of a subject is becoming in fact an increasingly widespread practice in order to perform prevention in subjects particularly at risk, in order to monitor constantly the vital physiological parameters in subjects with ascertained pathologies and in order to collect data and information useful to check the state of health of a subject.

Moreover, the appropriate combination of said vital physiological parameters allows to evaluate also the emotional state of a subject with respect to a sudden event, a cardiac effort or a state of discomfort or stress.

For an accurate analysis it is essential to perform more than one repetition of the detection of said vital physiological parameters, allowing, in this manner, a comparison with the previous detections in order to highlight a worsening, an improvement or a stability of the state of health of the subject being examined.

Recently, thanks to the continuous technological development in the health sector, there is a progressive change of the methods by means of which the subjects undergo medical treatments: there is, in fact, more and more a migration towards treatment management and monitoring of the personal state of health independent of the position occupied by the subject.

Currently, various devices are in use which allow a detection of vital physiological parameters of a subject, such as, for example, the heart rate, arterial oxygenation or breathing rate. In particular, these are devices that allow to improve the day-to-day management of specific pathologies and the monitoring of the state of health of a subject, facilitating self-care, i.e., a personal health treatment.

These devices, however, have drawbacks, which include in particular, a high degree of invasiveness, low portability and low quality of the acquired signal.

The aim of the present invention is to overcome the limitations of the background art described above, by devising a system and a method for detecting vital physiological parameters of a subject, particularly useful and practical in the healthcare sector, in the sports sector and in the automotive sector, which allow to obtain better results than the ones obtainable with known solutions.

Within this aim, an object of the present invention is to conceive a system and a method for detecting vital physiological parameters of a subject that provide, following at least one cardiac cycle, said vital physiological parameters.

Another object of the present invention is to devise a system and a method for detecting vital physiological parameters of a subject that provide said vital physiological parameters without the aid of pumping systems, oscillometric systems or tonometric systems.

A further object of the present invention is to conceive a system and a method for detecting vital physiological parameters of a subject that provide said vital physiological parameters even in the presence of movement of said subject.

Another object of the present invention is to devise a system and a method for detecting vital physiological parameters of a subject that provide said vital physiological parameters simultaneously.

A further object of the present invention is to conceive a system and a method for detecting vital physiological parameters of a subject that allow to calculate the vital physiological parameter related to systolic and diastolic arterial pressure (in short, the systolic and diastolic arterial pressure) on the basis of some parameters that can be identified by the electrocardiac signal (in short, ECG signal) and by the photoplethysmographic signal (in short, PPG signal).

Moreover, an object of the present invention is to devise a system and a method for detecting vital physiological parameters of a subject that allow to calculate the vital physiological parameter related to the breathing rate (in short, the breathing rate) by means of a processing of the PPG signal.

Another object of the present invention is to devise a system and a method for detecting vital physiological parameters of a subject that is highly reliable, relatively easy to provide and at competitive costs if compared with the background art.

This aim and these and other objects that will become better apparent hereinafter are achieved by a system and a method for detecting vital physiological parameters of a subject, comprising support means which can be associated with said subject and are connected to acquisition means configured to acquire synchronously an ECG signal and a PPG signal of said subject, and processing means connected to said acquisition means, said processing means comprising a systolic and diastolic arterial pressure module configured to calculate a vital physiological parameter related to systolic and diastolic arterial pressure, respectively, which can be transmitted to at least one telematic device by means of transceiver means configured to transmit said vital physiological parameter toward said telematic device.

Further characteristics and advantages of the invention will become better apparent from the description of a preferred but not exclusive embodiment of the system for detecting vital physiological parameters of a subject according to the invention, illustrated by way of nonlimiting example in the accompanying drawings, wherein.

Figure 1:
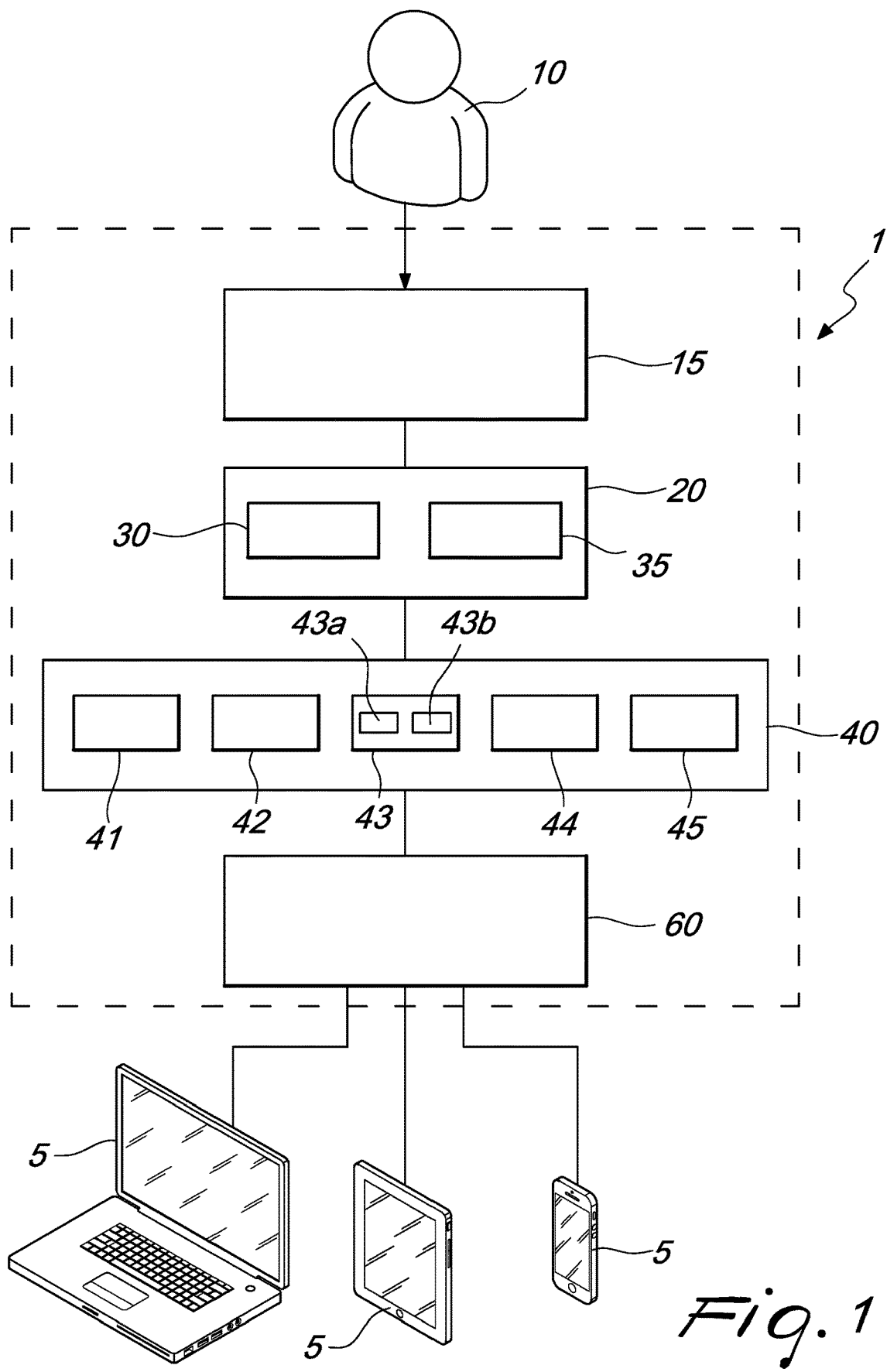
FIG. 1 is a block diagram that shows schematically a possible embodiment of the system for detecting vital physiological parameters of a subject, according to the present invention.

With reference to FIG. 1, the system for detecting vital physiological parameters of a subject according to the invention, designated generally by the reference numeral 1, comprises substantially support means 15, acquisition means 20, processing means 40 and transceiver means 60.

The support means 15 are shaped to allow said subject 10 to place parts of the body, arranged symmetrically with respect to the cardiac axis, on said support means. These support means 15 comprise, for example, bicycle and motorcycle handles, supports for fitness machines, supports inside the cabin of a vehicle or wearable accessories.

In particular, the system 1 can be applied to situations of anchoring to the human body in different areas, such as, for example, in the nape region by way of support means 15 that can be integrated in a helmet, in the ear region by way of support means 15 that can be integrated in a headset, in the waist region by way of support means 15 connected to a belt or in the chest region by way of support means 15 connected to an elastic bandage.

The acquisition means 20, connected to the support means 15, are configured to acquire synchronously an ECG signal and a PPG signal of said subject 10 according to the invention.

The acquisition means 20 comprise at least one electrocardiac acquisition card 30 adapted to acquire said ECG signal of said subject 10 and at least one photoplethysmographic card 35 adapted to acquire said PPG signal of said subject 10.

The electrocardiac acquisition card 30 is adapted to acquire said ECG signal of said subject 10 and to communicate with said photoplethysmographic acquisition card 35.

In one embodiment of the system 1 for detecting vital physiological parameters of a subject 10 according to the invention, the electrocardiac acquisition card 30 is configured to transform a superficial physiological signal caused by the depolarization and repolarization of the cardiac dipole into a signal of the electric type. The transformation from a superficial physiological signal, caused by the depolarization and repolarization of the cardiac dipole, to a signal of the electric type occurs by means of two components.

The first component comprises an electroionic interface (electrode) composed of a particular conductive fabric based on silver, capable of transforming ionic conduction into a corresponding electron current.

The second component comprises an instrumentation amplifier and a system for conditioning and recovering the direct-current component of the ECG signal. This conditioning and recovery system comprises a microcontroller, for example a Texas Instruments MSP430 microcontroller, which allows to provide effectively the digital filtering and the following of the direct-current component of the ECG signal in order to convert the analog signal into a digital signal.

The photoplethysmographic acquisition card 35 is adapted to acquire said PPG signal of said subject 10 and to communicate with said electrocardiac acquisition card 30.

In one embodiment of the system 1 for detecting vital physiological parameters of a subject 10 according to the invention, the photoplethysmographic acquisition card 35 comprises at least one sensor which acquires the variation of the light reflected by the vascularized tissue of peripheral microcirculation. This sensor is based on two LEDs, each with a different frequency emission (one in the visible range and one in the infrared range), and on a single receiving photodiode capable of receiving both frequencies. The signal received by the photodetector is transferred to the reading and conditioning circuit, which comprises a microcontroller, for example a Texas Instruments MSP430 microcontroller, which allows to provide effectively the filtering and following of the direct-current component of the PPG signal.

The processing means 40, connected to said acquisition means 20, comprise at least one module 41, 42, 43, 44, 45 adapted to calculate a respective vital physiological parameter.

In one embodiment of the system 1 for detecting vital physiological parameters of a subject 10 according to the invention, the processing means 40 communicate only with one between the electrocardiac acquisition card 30 and the photoplethysmographic acquisition card 35. In this manner, data transfer is minimized, obtaining the data collected by the acquisition means 20 by means of a dialog based on a proprietary communication protocol, a particular serial communication protocol. The processing means 40 are configured to use the so-called "multicore" architecture, which provides for the presence of at least two processors capable of processing the received data and providing said vital physiological parameters.

In particular, the processing means 20, such as for example a "Raspberry Pi" electronic board or a "C.H.I.P" electronic board, allow to apply a Loess (Local Regression) filter to the ECG signal and to the PPG signal, to process said ECG signal and said PPG signal by means of a processing system based on EMD (Empirical Mode Decomposition) and to select N functions that are intrinsically dependent on the signal (IMF, Intrinsic Mode Functions). These functions, deriving from the EMD decomposition, are then combined by the processing means 20 in order to obtain the signal from which to extract said vital physiological parameters.

In an embodiment of the system 1 for detecting vital physiological parameters of a subject 10 according to the invention, the cardiac module 41 allows to calculate the vital physiological parameter related to the heart rate (in short, the heart rate) by means of the analysis of the ECG signal.

In one embodiment of the system 1 for detecting vital physiological parameters of a subject 10 according to the invention, the respiration module 42 allows to calculate the vital physiological parameter related to the breathing rate (in short, the breathing rate). A processing of the PPG signal is performed, breaking down said PPG signal into a finite number of IMF and applying the Hilbert-Huang transform to each one of said intrinsically signal-dependent functions (IMF). One obtains as a result, for each one of the functions, the envelope and the instantaneous frequency. The sum of the envelopes of the functions the frequency of which is comprised in a range equal to 10-20 breaths per minute (equal to 0.17-0.42 Hz), which corresponds to the range over which the breathing rate of a human subject can vary, provides the profile of the breathing signal. The inverse value of the peak-to-peak period of said breathing signal generates the breathing rate (in breaths per minute).

Figure 2:
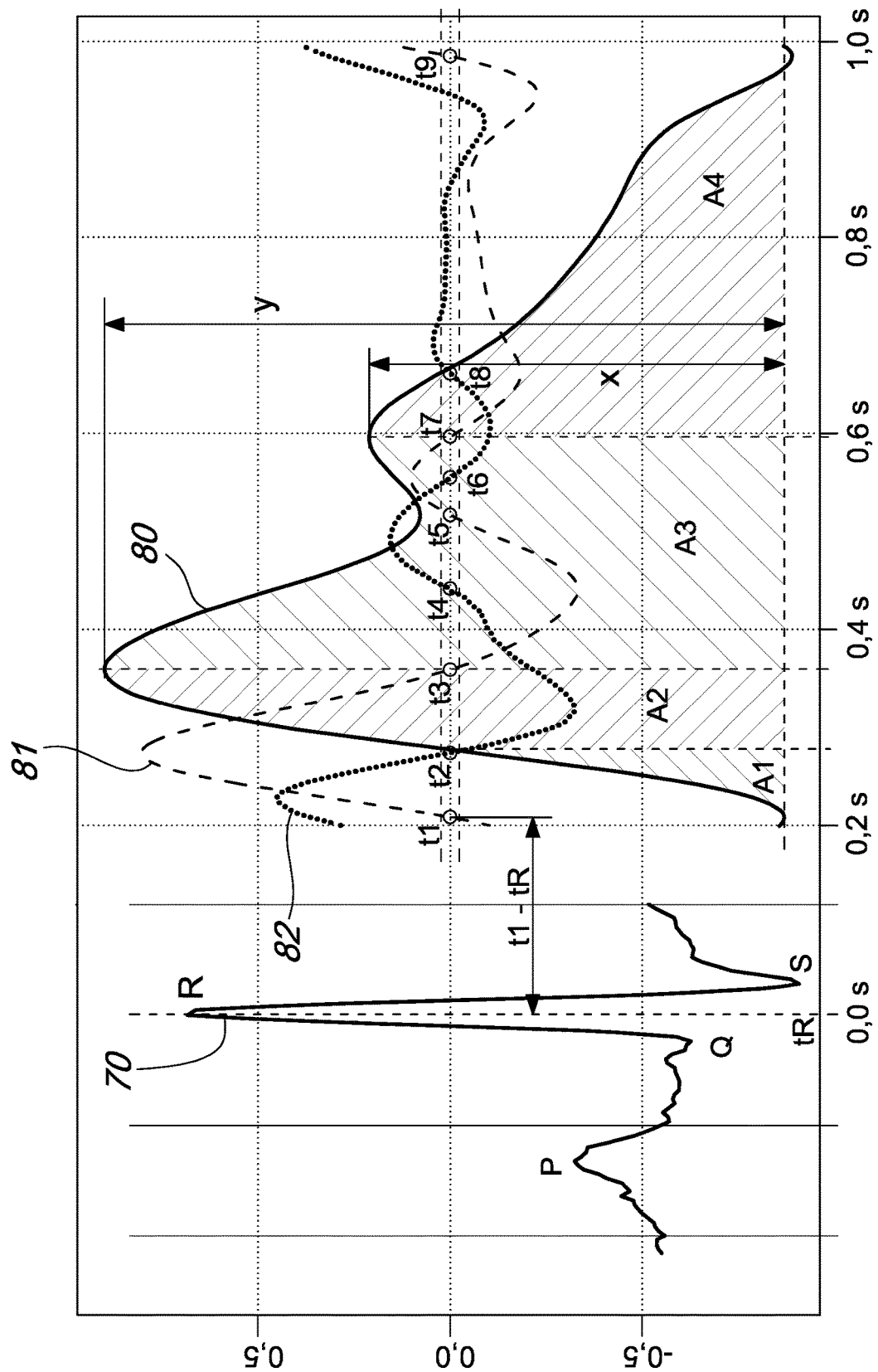
FIG. 2 shows the behavior over time of the ECG signal and of the PPG signal within a same chart, according to the present invention.

With reference to FIG. 2, the ECG signal 70 is characterized by various portions termed waves (P, Q, R, S), which repeat at each cardiac cycle. The origin of the temporal axis (tR=0 s) coincides with the occurrence of the wave R, which corresponds to the depolarization of the apex of the left ventricle. The parameters related to the PPG signal 80, to the first derivative of the PPG signal 81 and to the second derivative of the PPG signal 82 are evaluated as a function of the time tR of the wave R.

In one embodiment of the system 1 for detecting vital physiological parameters of a subject 10 according to the invention, the systolic and diastolic arterial pressure module 43 comprises a systolic arterial pressure module 43a adapted to calculate the systolic arterial pressure.

In one embodiment of the system 1 for detecting vital physiological parameters of a subject 10 according to the invention, the systolic and diastolic arterial pressure module 43 comprises a diastolic pressure module 43b adapted to calculate the diastolic arterial pressure.

Using the time intervals and the value of the areas described in FIG. 2, the systolic and diastolic arterial pressure module 43 generates two linear or nonlinear models, each represented by a linear or nonlinear equation, which expresses the value of, respectively, systolic or diastolic arterial pressure for each cardiac cycle synchronized with all the other vital parameters calculated in the various embodiments of the system 1, described hereinafter.

In particular, the systolic arterial pressure module 43a generates a linear or nonlinear model, represented by a linear or nonlinear equation, that expresses the systolic arterial pressure value, while the diastolic arterial pressure module 43b generates a linear or nonlinear model, represented by a linear or nonlinear equation, which expresses the diastolic arterial pressure value.

The final expression of the equation of each one of the two models is established, once and for all, with an optimization process which compares the systolic or diastolic pressure value for each cardiac cycle with the systolic or diastolic pressure value obtained from a reference calibrated method for clinical use. In this process, the systolic and diastolic arterial pressure module 43 modifies the coefficients of the equation until the minimum difference is reached between the pressure values obtained from the models and those obtained from the systolic and diastolic pressure reference method, all the values being expressed in mmHg. This optimization process offers a reliable result and can be repeated in order to improve the accuracy of the calculation of systolic and diastolic pressure. The 14 parameters related to FIG. 2 are as follows:

t1−tR=plet_origin (zero $1^{st}$ derivative);
t2−tR=plet_syst_max_slope (zero $2^{nd}$ derivative);
t3−tR=plet_systolic (zero $1^{st}$ derivative) or PTT (Pulse Transit Time), i.e., the time passing between the production of the wave R in the ECG signal and the maximum of the PPG signal. In particular, said PTT represents the propagation time of the cardiac impulse within the vascular system;
t4−tR=plet_syst_dicrotic_notch (zero $2^{nd}$ derivative);
t5−tR=plet_min_betw_syst_diast (zero $1^{st}$ derivative);
t6−tR=plet_diast_max_slope (zero $2^{nd}$ derivative);
t7−tR=plet_diastolic (zero $1^{st}$ derivative);
t8−tR=plet_diast_dicrotic_notch (zero $2^{nd}$ derivative);
t9−tR=plet_end (zero $1^{st}$ derivative);
A_I=x/y (augmentation index);
A1=area under PPG between t1 and t2;
A2=area under PPG between t2 and t3;
A3=area under PPG between t3 and t7;
A4=area under PPG between t7 and t9;

The systolic pressure value (Psist) is calculated by means of the following equation:

$$Psist = T1s \cdot (t1 - tR) + T2s \cdot (t2 - tR) + T3s \frac{1}{(t3 - tR)^2} + T4s \cdot (t4 - tR) +$$
$$T5s \cdot (t5 - tR) + T6s \cdot (t6 - tR) + T7s \cdot (t7 - tR) + T8s \cdot (t8 - tR) +$$
$$T9s \cdot (t9 - tR) + Ais\frac{x}{y} + Ar1s \cdot A1 + Ar2s \cdot A2 + Ar3s \cdot A3 + Ar4s \cdot A4$$

The values of the coefficients T1s-T9s, Ais and Ar1s-Ar4s are calculated by means of the optimization process, using the systolic pressure values measured in the examined subjects. The final values of these coefficients, calculated in the optimization process and combined with the parameters described earlier, provide the final form of the equation used by the device for calculating systolic pressure in real time.

The diastolic pressure value (Pdiast) is calculated by means of the following equation:

$$Pdiast = T1d \cdot (t1 - tR) + T2d \cdot (t2 - tR) + T3d \cdot (t3 - tR) + T4d \cdot (t4 - tR) +$$
$$T5d \cdot (t5 - tR) + T6d \cdot (t6 - tR) + T7d \cdot (t7 - tR) + T8d \cdot (t8 - tR) +$$
$$T9d \cdot (t9 - tR) + Aid\frac{x}{y} + Ar1d \cdot A1 + Ar2d \cdot A2 + Ar3d \cdot A3 + Ar4d \cdot A4$$

The values of the coefficients T1d-T9d, Ais and Ar1d-Ar4d are calculated by means of the optimization process, using the diastolic pressure values measured in the examined subjects. The final values of the coefficients, calculated in the optimization process and combined with the parameters described earlier, provide the final form of the equation used by the device for calculating diastolic pressure in real time.

In one embodiment of the system 1 for detecting vital physiological parameters of a subject 10 according to the invention, the thermal module 44 allows to calculate the vital physiological parameter related to body temperature (in short, body temperature) by means of at least one temperature sensor based on thermocouples.

In one embodiment of the system 1 for detecting vital physiological parameters of a subject 10 according to the invention, the arterial oxygenation module 45 allows to calculate the vital physiological parameter related to the arterial oxygenation (in short, arterial oxygenation) by means of an analysis of the PPG signal.

The above mentioned vital physiological parameters can be transmitted to at least one telematic device 5 by way of transceiver means 60.

The transceiver means 60 are configured to transmit the vital physiological parameters evaluated by the processing means 40 to the telematic devices 5, such as for example a personal computer, a smartphone or a server computer. The transmission of vital physiological parameters from the processing means 40 to the telematic devices 5 occurs by means of communication protocols such as, for example, the UART (Universal Asynchronous Receiver-Transmitter) protocol, the I$^2$C (Inter Integrated Circuit) protocol, the CanBus (Controller Area Network) protocol and the HTML (HyperText Markup Language) protocol.

In practice it has been found that the invention fully achieves the intended aim and objects. In particular, it has been shown that the system and the method for detecting vital physiological parameters of a subject thus conceived allow to overcome the quality limitations of the background art, since they allow to obtain better effects than those obtainable with known solutions, providing the vital physiological parameters of a subject after at least one cardiac cycle.

The system and the method according to the invention allow to determine the diastolic and systolic pressure values by synchronous detection of the ECG signal and of a single PPG signal. These signals are then processed and allow to determine, by means of two models, the diastolic pressure value and the systolic pressure value, without using any pneumatic cuff (cuffless) and any calibration procedure.

Detection of the ECG signal can occur for example by placing the subject's two hands on the device and the PPG signal can be detected from a finger of the subject.

Another advantage of the system and of the method for detecting vital physiological parameters of a subject according to the invention resides in that they allow to obtain said vital physiological parameters without the aid of pumping systems, oscillometric systems or tonometric systems.

A further advantage of the system and of the method for detecting vital physiological parameters of a subject according to the invention resides in that they provide said vital physiological parameters even in the presence of motion of said subject.

Another advantage of the system and of the method for detecting vital physiological parameters of a subject according to the invention resides in that they provide said vital physiological parameters simultaneously.

A further advantage of the system and of the method for detecting vital physiological parameters of a subject according to the invention resides in that they allow to calculate systolic and diastolic arterial pressure on the basis of some parameters that can be identified from the ECG signal and from the PPG signal.

Another advantage of the system and of the method for detecting vital physiological parameters of a subject according to the invention resides in that they allow to calculate the breathing rate by means of a processing of the PPG signal.

Although the system and the method for detecting vital physiological parameters of a subject according to the invention have been conceived particularly for use in the healthcare sector, in the sports sector or in the automotive sector, they can be used in any case more generally for detecting and monitoring personal vital physiological parameters.

The invention thus conceived is susceptible of numerous modifications and variations, all of which are within the scope of the appended claims. Furthermore, all the details may be replaced with other technically equivalent elements.

In practice, the materials used, so long as they are compatible with the specific use, as well as the contingent shapes and dimensions, may be any according to requirements and to the state of the art.

To conclude, the scope of the protection of the claims must not be limited by the illustrations or preferred embodiments shown in the description by way of example, but rather the claims must comprise all the characteristics of patentable novelty that reside in the present invention, including all the characteristics that would be treated as equivalents by the person skilled in the art.

The disclosures in Italian Patent Application no. 102017000031915, from which this application claims priority, are incorporated herein by reference.

Where technical features mentioned in any claim are followed by reference signs, those reference signs have been included for the sole purpose of increasing the intelligibility of the claims and accordingly such reference signs do not have any limiting effect on the interpretation of each element identified by way of example by such reference signs.

The invention claimed is:

1. A system for detecting vital physiological parameters of a subject, the system comprising:
    (a) support means configured to allow said subject to place the palms of both hands on said support means;
    (b) acquisition means, connected to said support means, said acquisition means comprising at least one electrocardiac acquisition card adapted to acquire an ECG signal from the palms of said subject when the palms of both hands of said subject are placed on said support means and at least one photoplethysmographic card adapted to acquire a PPG signal of said subject when a finger of said subject is placed on said support means, said acquisition means configured to synchronously acquire the ECG signal and the PPG signal of said subject, for each cardiac cycle when both hands and the finger of said subject are placed on said support means, wherein said system is configured to calculate a first derivative of said PPG signal and evaluate a parameter relating to the first derivative of said PPG signal, being referred to the R peak, origin of a time axis, and calculate a second derivative of said PPG signal and evaluate a parameter relating to the second derivative of said PPG signal, being referred to the R peak, origin of a time axis, of which said ECG signal is composed; and
    (c) processing means which are connected to said acquisition means, said processing means comprising:
        (i) a systolic and diastolic arterial pressure module configured to calculate the subject's systolic and diastolic arterial pressure based on the synchronously acquired ECG and PPG signals, wherein the systolic arterial pressure (Psist) is calculated using the equation $$Psist = T1s \cdot (t1 - tR) + T2s \cdot (t2 - tR) + T3s \frac{1}{(t3 - tR)^2} + T4s \cdot (t4 - tR) +$$
$$T5s \cdot (t5 - tR) + T6s \cdot (t6 - tR) + T7s \cdot (t7 - tR) + T8s \cdot (t8 - tR) +$$
$$T9s \cdot (t9 - tR) + Ais\frac{x}{y} + Ar1s \cdot A1 + Ar2s \cdot A2 + Ar3s \cdot A3 + Ar4s \cdot A4;$$

wherein the diastolic arterial pressure (Pdiast) is calculated using the equation $$Pdiast = T1d \cdot (t1 - tR) + T2d \cdot (t2 - tR) + T3d \cdot (t3 - tR) + T4d \cdot (t4 - tR) +$$
$$T5d \cdot (t5 - tR) + T6d \cdot (t6 - tR) + T7d \cdot (t7 - tR) + T8d \cdot (t8 - tR) +$$
$$T9d \cdot (t9 - tR) + Aid\frac{x}{y} + Ar1d \cdot A1 + Ar2d \cdot A2 + Ar3d \cdot A3 + Ar4d \cdot A4;$$

wherein:
    t1−tR=plet origin (zero $1^{st}$ derivative);
    t2−tR=plet syst max slope (zero $2^{nd}$ derivative);
    t3−tR=plet systolic (zero $1^{st}$ derivative) or PTT (Pulse Transit Time);
    t4−tR=plet syst dicrotic notch (zero $2^{nd}$ derivative);
    t5−tR=plet min betw syst diast (zero $1^{st}$ derivative);
    t6−tR=plet diast max slope (zero $2^{nd}$ derivative);
    t7−tR=plet diastolic (zero $1^{st}$ derivative);
    t8−tR=plet diast dicrotic notch (zero $2^{nd}$ derivative);
    t9−tR=plet end (zero $1^{st}$ derivative);

A_I=x/y (augmentation index);
A1=area under PPG between t1 and t2;
A2=area under PPG between t2 and t3;
A3=area under PPG between t3 and t7; and
A4=area under PPG between t7 and t9;
  (ii) a cardiac module configured to calculate the subject's heart rate based on the synchronously acquired ECG signal;
  (iii) a respiration module configured to calculate the subject's breathing rate based on the synchronously acquired PPG signal;
  (iv) a thermal module configured to calculate the subject's body temperature; and
  (v) an arterial oxygenation module configured to calculate the subject's arterial oxygenation based on the synchronously acquired PPG signal;
wherein the parameters for the equations are obtained from the ECG and PPG characteristics in each cardiac cycle, and wherein the coefficients derived from a linear or non-linear regression model;
  (d) transceiver means configured to transmit said vital physiological parameters to at least one telematics device;
  wherein said processing means simultaneously calculates the-vital physiological parameters comprising the subject's systolic and diastolic arterial pressure; the subject's heart rate; the subject's breathing rate; the subject's body temperature; and the subject's arterial oxygenation.

2. The system according to claim 1, wherein said support means is selected from the group consisting of bicycle handles, motorcycle handles, supports for fitness machines, or supports inside the cabin of a vehicle.

3. A method for detecting vital physiological parameters of a subject, the method comprising the steps of:
  synchronously acquiring the vital physiological parameters of said subject with the system according to claim 1; and
  transmitting said vital physiological parameters to a telematic device through a transceiver means.

* * * * *